United States Patent [19]

Harvey, Sr. et al.

[11] Patent Number: 4,881,898
[45] Date of Patent: Nov. 21, 1989

[54] METHOD OF FORMING AN ANATOMICAL OCCLUSAL SURFACE CONFIGURATION ON A TOOTH-LIKE MEMBER AND STAMP FOR USE IN CONNECTION THEREWITH

[76] Inventors: Arthur E. Harvey, Sr., Davis Ave., Rd. #2, Pawcatuck, Conn. 06379; Thomas J. Harvey, 64 Floral Park Blvd., Pawtucket, R.I. 02861; Donald H. Harvey, 233 Benham Rd., Apt. #4, Washington Bldg., Groton, Conn. 06340

[21] Appl. No.: 181,664

[22] Filed: Apr. 14, 1988

[51] Int. Cl.$^4$ .................................................. A61C 5/00
[52] U.S. Cl. ..................................... 433/215; 433/214; 433/34
[58] Field of Search ................... 433/141, 40, 71, 218, 433/219, 322, 214, 215

[56] References Cited

U.S. PATENT DOCUMENTS

| | | | |
|---|---|---|---|
| 1,518,825 | 12/1924 | Stock | 433/32 |
| 3,064,354 | 11/1962 | Pos | 433/214 |
| 4,449,936 | 5/1984 | Bayer | 433/214 |

*Primary Examiner*—Robert Peshock
*Attorney, Agent, or Firm*—Salter & Michaelson

[57] ABSTRACT

A method of applying an anatomical occlusal surface configuration to a formable tooth-like member includes the step of pressing a stamp having a complimentary anatomical surface configuration onto the occlusal surface of the tooth-like member. The method can be effectively utilized in fabricating dental crowns, and it virtually assures consistent occlusal surface quality while minimizing labor costs. The stamp includes a stamping portion having the complimentary anatomical surface thereon and a handle portion for manipulating the stamping portion to form an occlusal surface on a tooth-like member.

9 Claims, 1 Drawing Sheet

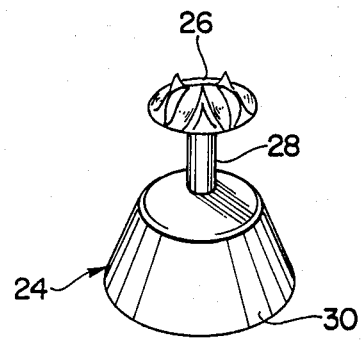
FIG. 1
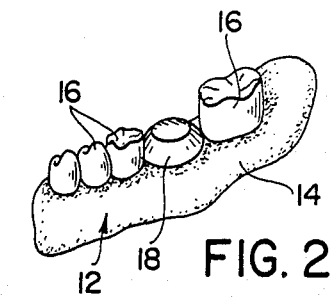
FIG. 2
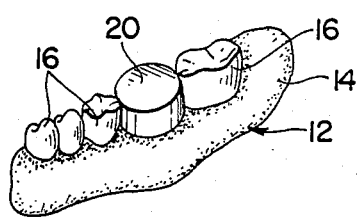
FIG. 3
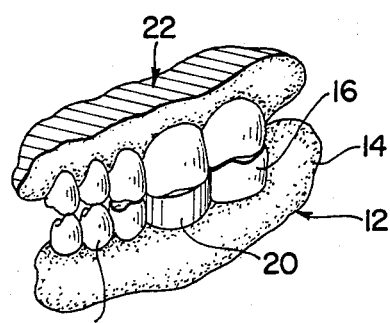
FIG. 4
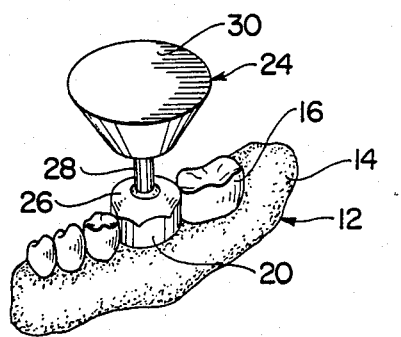
FIG. 6
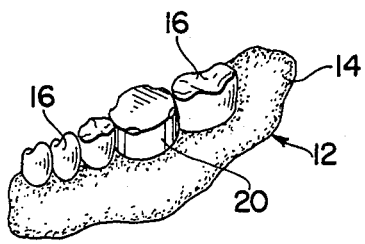
FIG. 5
FIG. 7

METHOD OF FORMING AN ANATOMICAL OCCLUSAL SURFACE CONFIGURATION ON A TOOTH-LIKE MEMBER AND STAMP FOR USE IN CONNECTION THEREWITH

BACKGROUND AND SUMMARY OF THE INVENTION

The instant invention relates to the field of dentistry and more particularly to a method of forming a tooth-like member having a shaped anatomical surface there.

Dental crowns have been widely used for many years to restore partially decayed or otherwise damaged teeth in the mouths of patients. In this connection, most dental crowns are made from molds or forms taken by dentists from the mouths of patients, and they are installed in the mouths of patients by dentists. However, for practical reasons, most crowns are actually fabricated in dental laboratories by laboratory technicians, although in some instances crowns are actually fabricated in the mouths of patients by dentists by applying dental composite materials over existing natural teeth.

The most common procedure for forming and installing a crown in the mouth of a patient is for a dentist to first form a mold of an existing tooth to which the crown is to be applied and to then prepare the existing tooth by removing the outer portions thereof in a grinding procedure to provide a prepared tooth of reduced size which is adapted to provide a base structure for receiving the crown thereon. A second mold is then taken of the prepared tooth, and thereafter the two molds are used to form a gold, metal, porcelain or castable ceramic crown which is dimensioned and configured to be received on the prepared tooth in the mouth of the patient. Finally, the finished crown is cemented to the prepared tooth to provide a restoration in the mouth of the patient which closely resembles the patient's original tooth.

Heretofore, one of the most common techniques for forming a dental crown has been to first form a wax pattern of the crown and to then form a gold, metal or castable ceramic crown from the wax pattern. In this connection, in order to form a wax pattern, a plaster or stone dye is first formed of the prepared tooth from a mold thereof taken from the patient's mouth, and a quantity of wax is applied to the dye to provide a wax form which has the general size and configuration of the desired crown. Next, a biting surface is established on the wax form by meshing it with an opposing model tooth, an occlusal surface is carved in the wax form which resembles the anatomy of a natural tooth, and buckle, lingual, mesial and distal surfaces are carved and shaped in the form to provide a finished wax pattern which resembles the patient's natural tooth. Thereafter, a casting investment is formed around the wax pattern, the wax is burned from the investment, forming a void which is cast with gold, an approved metal, or castable ceramic, and the crown is polished or colored to provide a finished crown which can be assembled in the mouth of the patient by the dentist.

As an alternative to the above procedure, a crown can be made directly in a ceramic construction by first applying a metal coping to a die formed from a mold of the patient's prepared tooth. Thereafter, a formable porcelain or ceramic composition is applied to the metal coping and formed in the general configuration of the desired crown. A biting surface is then established on the porcelain or ceramic form, an occlusal surface is carved in the porcelain or ceramic form, and buckle, lingual, mesial and distal surfaces are also carved and formed in the porcelain or ceramic form. Finally, the form is fired and polished to provide a crown which has the general configuration of the patient's natural tooth.

While the above methods have generally been found to be effective for forming dental crowns, they have also been found to be relatively time consuming, and they have been found to require relatively high-skilled labor. Specifically, it has been found that it is generally extremely time consuming to carve anatomical surface configurations in the occlusal surfaces of wax, porcelain or ceramic forms for dental crowns.

The instant invention provides an improved method of forming a dental crown which does not require a time consuming, hand carving procedure to form an anatomical occlusal surface on the crown. Specifically, the instant invention provides an improved method of forming a tooth-like member having an anatomical occlusal surface configuration. Still more specifically, the preferred method of the instant invention comprises the steps of applying a formable material to a prepared tooth or a die thereof, establishing a biting surface in the formable material by meshing it with an opposing tooth, and pressing an occlusal surface having an anatomical configuration into the formable material utilizing a stamp having a complimentary anatomical surface pattern thereon. The preferred method further comprises the step of forming and shaping buckle, lingual, mesial and distal surfaces in the formable material in order to form it into a tooth-like member. The method of the subject invention can be effectively carried out to fabricate wax patterns, and it can also be applied directly to curable porcelain or ceramic composite materials in order to form dental crowns. When the method is applied to fabricate a wax pattern, a stamp, either cold or slightly heated, having an anatomical surface configuration thereon is pressed onto a warm, soft wax form in order to impart the desired occlusal surface configuration to the wax form. On the other hand, when the method is applied directly to a curable dental composite material, a nontoxic release agent, such as a vegetable oil, is preferably applied to the stamp before it is pressed onto the composite material so that the stamp can be more easily released. In any event, the method can be effectively utilized to form various tooth-like members; although, obviously, a different anatomical stamp must be utilized for each different type of tooth in order to form the appropriate occlusal surface configuration thereon.

It has been found that the method of the instant invention can be effectively utilized for forming dental crowns having anatomical occlusal surface configurations of consistently high quality and that it represents a significant advancement over the heretofore available methods of forming anatomical surface configurations. Specifically, it has been found that extremely well sculptured surface configurations can be quickly and easily applied to the occlusal surfaces of tooth like members by even relatively unskilled labor utilizing the method of the instant invention. Hence, the method of the instant invention makes it possible to substantially reduce the labor costs involved in the manufacturing of dental crowns, and it also makes it possible to assure consistently high quality in the occlusal surface configurations of dental crowns.

As a result of the above, it is a primary object of the instant invention to provide an effective method of forming an anatomical occlusal surface on a tooth-like member.

Another object of the instant invention is to provide an improved method of forming a dental crown.

An even further object of the instant invention is to provide a method of forming a dental crown which does not require skilled carving operations to form an anatomical configuration on the occlusal surface of the crown.

Other objects, features and advantages of the invention shall become apparent as the description thereof proceeds when considered in connection with the accompanying illustrative drawings.

DESCRIPTION OF THE DRAWINGS

In the drawings which illustrate the best mode presently contemplated for carrying out the present invention:

FIG. 1 is an enlarged perspective view of the stamp utilized in the method of the instant invention; and FIGS. 2-7 are sequential views illustrating the method of the instant invention as it is applied to forming a dental crown.

DESCRIPTION OF THE INVENTION

Referring now to the drawings, the method of the instant invention is illustrated in FIGS. 2-7. In this connection, the method can be effectively applied to simply and accurately form a shaped anatomical occlusal surface on a tooth-like member which may be either a wax pattern for a dental crown, an uncured porcelain or ceramic dental crown, or an uncured composite resin crown.

Referring now more specifically to the drawings, the method of the instant invention as it is applied to forming a wax pattern 10 for a dental crown is illustrated in FIGS. 2-7. In this connection, the wax pattern 10 is formed on a plaster model generally indicated at 12 which has previously been formed in accordance with conventional dental molding techniques to resemble the configuration of the lower left jaw and tooth structure of a patient. The plaster model 12 includes a jaw portion 14, a plurality of molded teeth 16, and a die 18 having the configuration of a tooth which has been prepared to receive a dental crown thereon. In the first step of the method, a quantity of formable dental wax is applied to the die 18 to form a wax form 20 having the general size and configuration of the desired crown. Thereafter, as illustrated in FIG. 4, a complimentary model 22 of an upper jaw and tooth structure is positioned in engagement with the teeth 16 and the wax form 20 in order to establish a biting surface on the wax form 20 as illustrated in FIG. 5. Thereafter, as illustrated in FIG. 6, a stamp 24 is pressed onto the occlusal surface of the wax form 20 in order to form a shaped anatomical surface configuration in the occlusal surface of the wax form 20. In this connection, the stamp 24 is preferably made from a suitable, corrosion-resistant metal; and, as illustrated in FIG. 1, it comprises a stamping portion 26 which is attached to one end of a shaft 28 and a handle portion 30 which is attached to the opposite end of the shaft 28. The stamping portion is formed in a complimentary configuration to the occlusal surface of a normal healthy tooth; and, accordingly, by pressing the stamping portion 26 onto the occlusal surface of the form 20 an anatomical surface configuration can be effectively applied to the occlusal surface thereof. In this regard, the cold or slightly heated stamping portion 26 is pressed into warm, soft wax so that it leaves an impression in the wax form 20 in order to more effectively impart a configuration thereto which is complimentary to that of the stamping portion 26. It will be understood, however, that the stamp 24 is adapted to impart a specific anatomical surface configuration to the wax form 20 and that other similar stamps must be utilized to form anatomical surface configurations in the occlusal surfaces of other teeth. In any event, after an occlusal surface has been applied to the form 20 with the stamp 24, buckle, lingual, mesial and distal surfaces are carved and shaped into the form 20 by conventional techniques to produce the finished wax pattern 10 which may then be utilized for forming a full cast gold, metal, porcelain or castable ceramic crown by conventional techniques.

A similar technique to that hereinabove described can be utilized to directly form a porcelain fused to gold or metal dental crown in accordance with the method of the subject invention. More specifically, in order to directly form a dental crown, a metal coping is applied to a die of a prepared tooth, such as the die 18, and a dental ceramic or porcelain material is applied in a formable consistency to the metal coping on the die to form a ceramic or porcelain form of the desired crown. Thereafter, a biting surface is established on the porcelain or ceramic form utilizing an opposing model of a jaw and tooth structure and a shaped occlusal surface is pressed into the form utilizing a stamp, such as the stamp 24. Thereafter, the porcelain or ceramic form is further shaped by conventional techniques to form buckle, lingual, mesial and distal surfaces thereon. Finally, the uncured crown is removed from the die and fired or otherwise cured according to conventional techniques and polished to provide a finished crown which is ready to be installed in the mouth of a patient by a dentist.

A similar technique can also be utilized to directly form a crown on a prepared tooth in the mouth of a patient by the dentist. Specifically, a crown can be applied directly to a prepared tooth by first applying a formable dental composite material, such as a self-cured or light-cured composite resin directly to the prepared tooth to provide an uncured composite form in the mouth of the patient. Thereafter, a biting surface is applied to the composite form by engaging it with the opposing tooth or teeth in the mouth of the patient. In this regard, it has been found that it is preferable to overlay a thin sheet of material, such as a wet cellophane, on the composite form before establishing a biting surface thereon so that the composite material does not stick to the opposing tooth or teeth, the sheet of material being removed from the composite form after the biting surface has been established. A shaped anatomical occlusal surface configuration is then stamped into the form utilizing a stamp, such as the stamp 24. In this connection, prior to applying a stamp to the composite form, the stamp is preferably coated with a suitable nontoxic release agent, such as a vegetable oil, in order to prevent it from sticking to the composite material. In any event, after the desired anatomical surface configuration has been applied to the composite form, the form is further shaped by conventional techniques to apply the desired buckle, lingual, mesial and distal surface configurations thereto, and the composite form is cured by conventional techniques to produce a finished crown. Thereafter, final adjustments are made to the patient's bite in a conventional manner.

It is seen therefore, that the instant invention provides an effective method of forming an anatomical surface on a tooth-like member and that it also provides an effective method of forming a dental crown having a shaped anatomical occlusal surface configuration. In this connection, it has been found that by utilizing a stamp having a complimentary anatomical configuration, it is possible to quickly, accurately and reliably impart an anatomical surface configuration to an occlusal surface of a tooth-like member. Further, it has been found that by utilizing a stamp to apply an anatomical surface configuration to a tooth-like member, the occlusal surface of the tooth-like member can be formed in a relatively short period of time by even a relatively unskilled worker. As a result of these advantages, the method of the the instant invention is felt to represent a significant advancement in the art which has substantial commercial merit.

While there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed is:

1. A method of forming an anatomical occlusal surface in a formable tooth-like member comprising the steps of:
   (a) establishing a partially formed occlusal surface in said tooth-like member by meshing it with an opposing tooth, said partially formed occlusal surface including a biting surface but not including an anatomical surface pattern;
   (b) separating said tooth-like member with said partially formed occlusal surface thereon from said opposing tooth; and
   (c) pressing an anatomical surface configuration into said partially formed occlusal surface utilizing a rigid anatomical stamp having a predetermined complimentary anatomical occlusal surface configuration thereon, said stamp being formed without complimentary buckle, lingual, mesial and distal side surface portions and being pressed onto said tooth-like member so as to impart an anatomical surface configuration to said partially formed occlusal surface without significantly altering the configurations of the buckle, lingual, mesial and distal side surface portions of said tooth-like member.

2. In the method of claim 1, said tooth-like member further characterized as a wax pattern, said pressing step further characterized as pressing an anatomical surface configuration into said wax pattern utilizing a heated stamp having a complimentary anatomical occlusal surface configuration.

3. In the method of claim 2, said opposing tooth further characterized as an opposing tooth model.

4. In the method of claim 1, said formable tooth-like member further characterized as comprising a curable dental composite material on a prepared natural tooth.

5. In the method of claim 4, said pressing step further characterized as pressing said anatomical occlusal surface configuration into said tooth-like member utilizing a stamp having a release agent thereon.

6. In the method of claim 5, said release agent comprising a vegetable oil.

7. In the method of claim 1, said tooth-like member comprising a prepared tooth model having a metal coping thereon, and a formable dental ceramic material on said metal coping.

8. The method of claim 7 further comprising the step of curing said tooth-like member.

9. A stamp for forming an anatomical occlusal surface in a formable tooth-like member comprising a rigid stamping portion having an occlusal stamping surface thereon, said occlusal stamping surface having a configuration which is complimentary to the anatomical occlusal surface configuration of a single natural tooth and a handle portion on said stamping portion for manipulating the latter to press said stamping surface onto said formable tooth-like member in order to impart an anatomical occlusal surface configuration thereto, said stamping portion not including buckle, lingual, mesial and distal surface portions and being engageable with said formable tooth-like member to impart an anatomical occlusal surface configuration thereto without engaging the buckle, lingual, mesial and distal side surface portions of said tooth-like member.

* * * * *